United States Patent
Adams et al.

(10) Patent No.: US 7,347,843 B2
(45) Date of Patent: *Mar. 25, 2008

(54) VASCULAR ACCESS PORT WITH NEEDLE DETECTOR

(75) Inventors: H. Clark Adams, Arden Hills, MN (US); Brian P. Brockway, Shoreview, MN (US); Perry A. Mills, Arden Hills, MN (US)

(73) Assignee: Transoma Medical, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/190,789

(22) Filed: Jul. 26, 2005

(65) Prior Publication Data

US 2005/0256451 A1   Nov. 17, 2005

Related U.S. Application Data

(63) Continuation of application No. 10/246,324, filed on Sep. 17, 2002, now Pat. No. 6,962,580.

(51) Int. Cl.
*A61M 31/00* (2006.01)
(52) U.S. Cl. .................................. 604/288.02
(58) Field of Classification Search ............. 604/891.1, 604/93.01, 175, 288.01, 288.02, 288.04, 604/890.1; 324/207.2; 73/DIG. 3, 514.31
See application file for complete search history.

(56) References Cited

U.S. PATENT DOCUMENTS 4,573,994 A   3/1986   Fischell et al.
4,804,054 A * 2/1989   Howson et al. ............. 128/898
4,846,191 A   7/1989   Brockway et al.
5,387,192 A   2/1995   Glantz et al.
5,487,760 A   1/1996   Villafana
5,522,394 A   6/1996   Zurbrugg
5,535,752 A   7/1996   Halperin et al.
6,033,366 A   3/2000   Brockway et al.
6,122,536 A   9/2000   Sun et al.
6,285,897 B1  9/2001   Kilcoyne et al.

(Continued)

FOREIGN PATENT DOCUMENTS

WO   WO 00/16686 A2   3/2000

OTHER PUBLICATIONS

*Clinician Information* Port-A-Cath® and Port-A-Cath II® Implantable Venous Access Systems / P.A.S. Port Implantable Peripheral Venous Access Systems, Smiths Industries Medical Systems, SIMS Deltec, Inc., St. Paul, MN 55112, USA pp. 1-24.

(Continued)

*Primary Examiner*—Kevin C. Sirmons
*Assistant Examiner*—Catherine N. Witczak
(74) *Attorney, Agent, or Firm*—Fish & Richardson P.C.

(57) ABSTRACT

A vascular access port system including means for detecting and indicating the presence or absence of a needle. The detecting and indicating means may be carried in whole or in part by one of or both of the needle and/or the vascular access port. The detecting and indicating means may utilize a conductive needle, a mechanical switch, a magnetic switch, a Hall effect sensor, an electric field, a magnetic field, or an inductor, for example, for detection purposes. The vascular access port system permits the practitioner to confirm that the needle has been correctly inserted into the VAP, and notifies the patient and/or practitioner if the needle has been accidentally withdrawn.

18 Claims, 4 Drawing Sheets

U.S. PATENT DOCUMENTS 6,296,615 B1    10/2001    Brockway et al.
6,740,076 B2 *   5/2004    Hoben et al. ............ 604/891.1
6,962,580 B2 *  11/2005    Adams et al. ........... 604/891.1

OTHER PUBLICATIONS

*System Information* Port-A-Cath® and Port-A-Cath II® Implantable Venous Access Systems / P.A.S. Port Implantable Peripheral Venous Access Systems, Smiths Industries Medical Systems, SIMS Deltec, Inc., St. Paul, MN 55112, USA, 12 pages total.

U.S. Appl. No. 10/077,566, filed Feb. 15, 2002, entitled *Devices, Systems and Methods for Endocardial Pressure Measurement* pp. 1-67.

U.S. Appl. No. 10/246,348, filed Sep. 17, 2002, entitled *Vascular Access Port With Physiological Sensorr* pp. 1-35.

* cited by examiner

VASCULAR ACCESS PORT WITH NEEDLE DETECTOR

This application is a continuation of U.S. patent application Ser. No. 10/246,324, filed Sep. 17, 2002, issued Nov. 11, 2005 as U.S. Pat. No. 6,962,580.

BACKGROUND OF THE INVENTION

The present invention generally relates to vascular access ports. In particular, the present invention relates to vascular access ports having means for needle detection.

Implantable vascular access ports (VAP) are used extensively in the medical field when recurrent infusions of therapeutic agents into a patient's circulatory system are required over extended periods of time. Such VAPs generally include a housing containing a reservoir and septum, with a catheter extending from the housing. The VAP housing is implanted in a subcutaneous pocket at an accessible location such as the arm, and the catheter extends from the housing to a remote vascular location to provide convenient, repeatable access to the patient's venous or arterial system deep in the body. In the subcutaneous pocket, the septum of the VAP may be pierced by a needle that is coupled via appropriate tubing to a therapeutic agent source in an intravenous bag or infusion pump, for example, so that the therapeutic agents may be administered. Such a vascular access system may be used in the home or other outpatient settings, as well as inpatient hospital settings.

Because the VAP resides in a subcutaneous pocket, it is not visible to the naked eye, with the exception of a slight contour that may be seen and felt on the skin overlaying the VAP. However, palpitation of the skin contour does not readily discern the septum of the VAP, and it is not possible to visually confirm with certainty that a needle has been correctly inserted through the septum and into the internal reservoir of the VAP. Thus, it is not uncommon for the health care practitioner to err when inserting the needle. An improperly inserted needle may result in the infusion of a drug into the subcutaneous space around the VAP. Once in the subcutaneous space, the drug may cause the patient pain and suffering, and with some drugs, even severe tissue necrosis. Presently, careful palpitation is the standard method used by practitioners to identify a properly inserted needle, and this method is susceptible to error.

Another significant problem with conventional VAPs is inadvertent removal of the needle from the VAP during infusion. Drug infusions are typically administered over a long period of time (relative to a single injection), and are sometimes performed outside a hospital setting. The needle may be secured to the skin over the VAP by adhesive tape, for example, so that the patient or nurse doesn't need to manually hold the needle in place. Once the needle is secured, the patient often moves around, whether it be slight movements in a recliner or bed, or more significant movements in attending to daily activities. Such movements may cause the infusion tubing to pull on the needle, potentially causing the needle to be inadvertently removed from the VAP. When this occurs, the patient and/or the nurse may be unaware of the accidental removal, and the infusion pump may continue to administer the drug. Thus, the patient may not receive the prescribed dosage and it may be difficult to determine exactly how much of the dosage was delivered to the patient before the needle was accidentally removed from the VAP.

Thus, there is a need for a VAP system that permits the practitioner to confirm that the needle has been correctly inserted through the septum and into the internal reservoir of the VAP, and a VAP system that notifies the patient and/or practitioner if the needle has been accidentally withdrawn.

BRIEF SUMMARY OF THE INVENTION

To address these needs and others, the present invention provides, in several exemplary embodiments, VAP systems for detecting the presence or absence of a needle. The systems generally include a means for detecting and indicating the presence or absence of a needle extending into the reservoir of the VAP. The detecting and indicating means may be carried in whole or in part by one of or both of the needle and/or the VAP. The detecting and indicating means may utilize a conductive needle, a mechanical switch, a magnetic switch, a Hall effect sensor, an electric field, a magnetic field, or an inductor, for example, to detect the needle. The detecting and indicating means may generate an indicator signal indicative of the presence and/or absence of the needle in the reservoir of the VAP, and may provide feedback to an infusion pump or the like. Thus, the present invention provides, in these exemplary embodiments, VAP systems that permit the practitioner to confirm that the needle has been correctly inserted into the VAP, and that notify the patient and/or practitioner if the needle has been accidentally withdrawn.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1A:
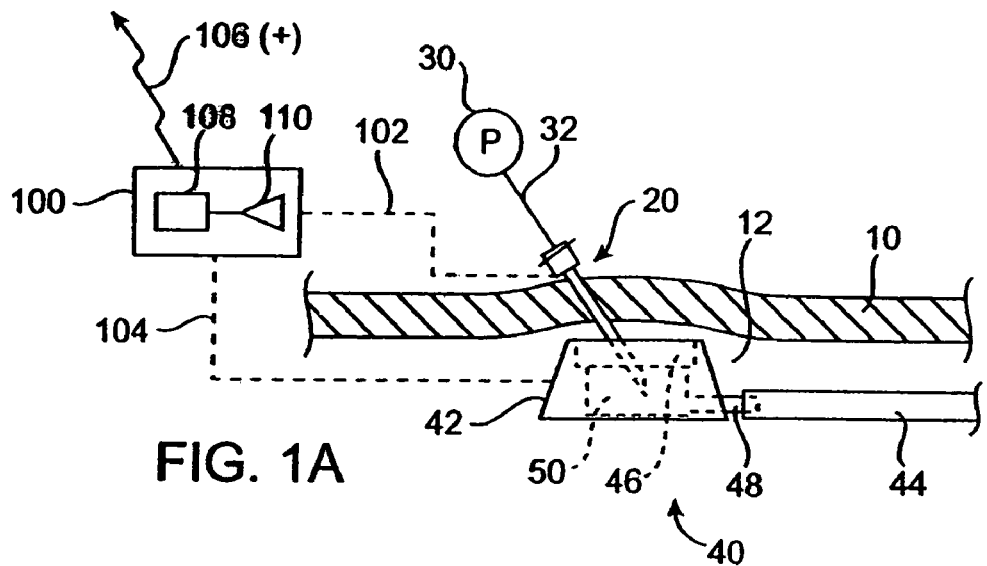
FIG. 1A is a schematic illustration showing a needle properly inserted into a vascular access port disposed under a patient's skin, wherein a detecting and indicating circuit generates a signal indicative of the needle being properly inserted into the vascular access port.

With reference to FIG. 1A, a schematic plan view of a needle 20 connected to a pressurized fluid source 30 by fluid connection 32. Pressurized fluid source 30 may comprise an infusion pump or syringe, for example. The needle 20 is shown properly inserted into a vascular access port (VAP) 40 disposed under a patient's skin 10. A needle detecting and indicating circuit 100 is connected to the needle 20 by functional link 102, and connected to the VAP 40 by functional link 104. The needle detecting and indicating circuit 100 may include separate or integral detecting 110 and indicating 108 circuits. The detecting circuit 108 detects the proximity or position of the needle 20 with respect to the VAP 40 and generates a detection signal as a function thereof, and the indicating circuit 108 includes a transducer that generates an indicator signal 106 as a function of the detection signal.

The indicating circuit 108 may include a comparator which compares the detection signal to a threshold signal value that is indicative of the needle 20 extending into the reservoir 50. The transducer in the indicating circuit 108 may generate the indicator signal 106 when the detection signal exceeds or falls below the threshold signal value, which is indicative of the needle being properly or improperly, respectively, inserted into the VAP 40.

Figure 1B:
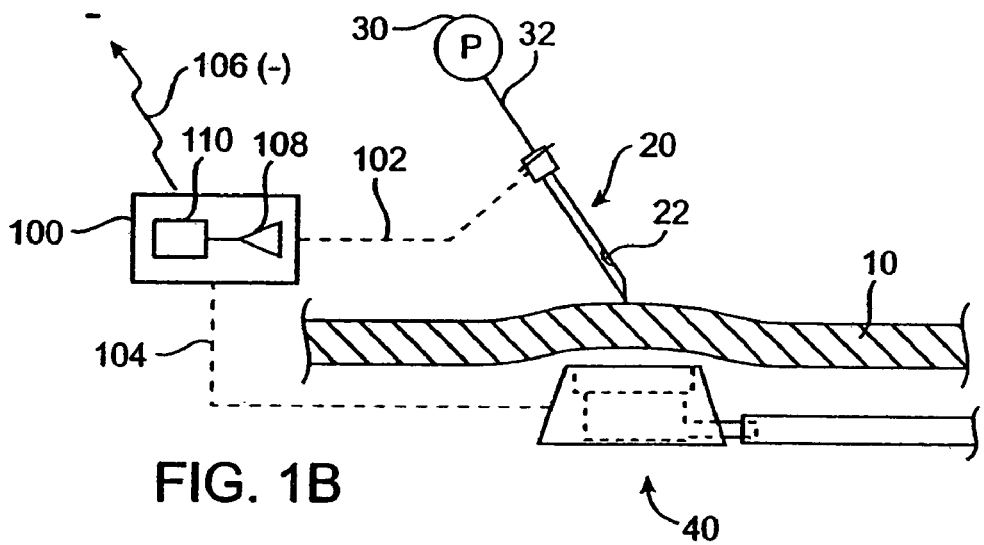
FIG. 1B is a schematic illustration showing the needle prior to insertion into the vascular access port, wherein the detecting and indicating circuit generates a signal indicative of the needle not being inserted into the vascular access port.
Figure 1C:
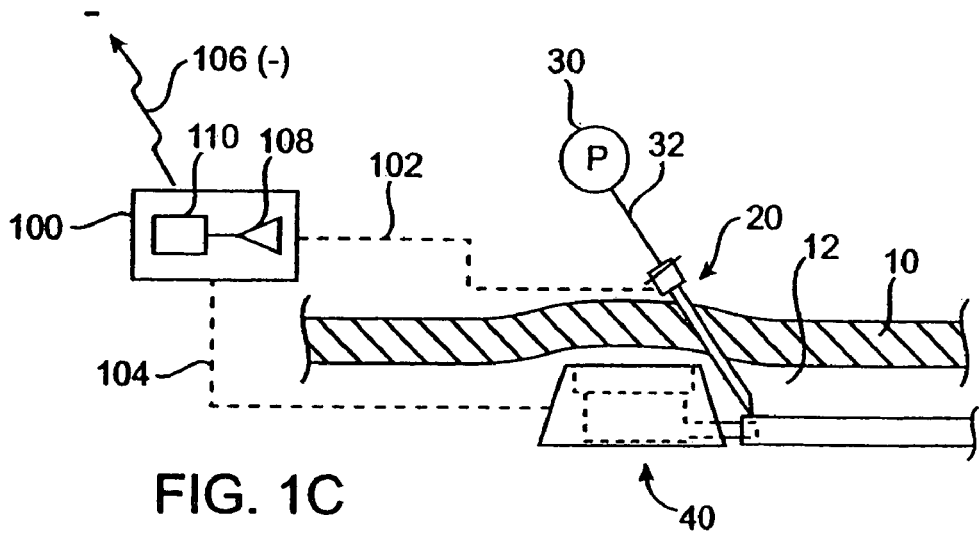
FIG. 1C is a schematic illustration showing the needle improperly inserted into a subcutaneous space around the vascular access port, wherein the detecting and indicating circuit generates a signal indicative of the needle not being properly inserted into the vascular access port.

For example, the indicator signal 106 may be indicative of the needle being properly inserted into the VAP 40 as shown in FIG. 1A. In addition or in the alternative, the indicator signal 106 may be indicative of the needle 20 not being inserted into the VAP 40, such as when the needle 20 is in position for insertion into the VAP 40 or has been accidentally removed therefrom as shown in FIG. 1B, or when the needle 20 is improperly inserted into the subcutaneous space 12 around the VAP 40 as shown in FIG. 1C.

The indicator signal 106 may be audible, visible, tactile, or a combination thereof. The indicator signal 106 may be generated by a transducer contained in indicating circuit 108. For purposes of distinction, an indicator signal 106 indicative of a properly inserted needle 20 is shown as a positive signal 106(+), and an indicator signal 106 indicative of an uninserted or improperly inserted needle 20 is shown as a negative signal 106(−). The positive indicator signal 106(+) may comprise a signal different from the negative indicator signal 106(−) or the absence of the negative indicator signal 106(−). Similarly, the negative indicator signal 106(−) may comprise a signal different from the positive indicator signal 106(+) or the absence of the positive indicator signal 106(+). The negative indicator signal 106(−) may comprise an alarm indicative of the needle 20 being accidentally removed from the VAP 40 after the needle 20 has been properly inserted into the VAP 40.

The indicator signal 106 may, in addition or in the alternative, provide feedback to the infusion pump 30 by a suitable connection (not shown). For example, the positive indicator signal 106(+) may provide feedback to the infusion pump 30 to start the administration of drugs, and the negative indicator signal 106(−) may provide feedback to the infusion pump 30 to stop the administration of drugs.

The needle detecting and indicating circuit 100 is shown schematically to illustrate its function, as opposed to its particular manifestation as will be described with reference to FIGS. 2-8. The needle detecting and indicating circuit 100 may be implanted in whole or in part. The needle detecting and indicating circuit 100 may be carried in whole by one of the needle 20 and the VAP 40, or carried in part by one or both of the needle 20 and the VAP 40. The exemplary associations shown between the needle 20 and the VAP 40 and the corresponding portions of the needle detecting and indicating circuit 100 may be reversed.

The functional links 102/104 are also shown schematically to illustrate the functional relationship between the detecting and indicating circuit 100 and the needle 20 and VAP 40, respectively. If the needle detecting and indicating circuit 100 is carried in part by both the needle 20 and the VAP 40, two functional links 102/104 may be used. If the needle detecting and indicating circuit 100 is carried by either (i.e., one of) the needle 20 or the VAP 40, only one of the functional links 102/104 is necessary. The functional links 102/104 may vary depending on, for example, where the detecting and indicating circuit 100 is disposed relative to the needle 20 and the VAP 40. For example, the links 102/104 may represent direct (e.g., wired) or indirect (e.g. wireless) connections.

The needle 20 may comprise a conventional hypodermic or infusion needle, modified to accommodate the particular detection scheme utilized as described with reference to FIGS. 2-8. The needle 20 may typically have a distal tip opening as shown in FIG. 1A, but may incorporate a side opening 22 as shown in FIG. 1B if the distal tip is used for detection purposes or would otherwise become obstructed upon insertion into the VAP 40. The needle 20 may be connected by fluid line 32 to a pressurized fluid source 30 such as a conventional syringe or infusion pump.

The design of the needle 20 may be modified to accommodate the particular detection scheme utilized, or the needle 20 may carry a separate component to accomplish the same. The following needle 20 design aspects are given by way of example, not limitation. For mechanical switch detection schemes, the needle 20 may comprise a rigid polymeric or metal material having sufficient column strength to activate the switch. For conduction and electric field detection schemes, the needle 20 may comprise an electrically conductive material such as stainless steel. If a conductive septum is utilized, the electrically conductive material of the needle 20 may be covered by insulation, leaving only the tip exposed. In this latter case, the conductive septum induces voltage in the needle 20, but only the tip of the needle 20 is directly exposed to the drug in the reservoir, thereby reducing potential adverse effect thereon.

For induction detection schemes, the needle 20 may comprise a magnetically permeable material such as a stainless steel with sufficient ferrous content. For Hall effect and magnetic switch schemes, the needle 20 may comprise a magnetized material such as stainless steel with sufficient ferrous content, and may be made magnetic by carrying a tubular permanent magnet, by prolonged exposure to a magnetic field, or by a coil winding producing an electromagnet, for example.

The VAP 40 is shown schematically and may comprise a variety of vascular access port designs (single or dual port) known to those skilled in the art, with certain modification as described in more detail hereinafter. In the illustrated embodiment, the VAP 40 includes a portal housing 42 and an elongate tubular infusion catheter 44 extending therefrom. The housing 42 may be implanted in a subcutaneous space 12 disposed below the patient's skin 10, with the infusion catheter 44 inserted into the patient's vascular system (not shown).

An internal reservoir 50 is contained within the housing 42 of the VAP 40. The housing 42 includes two openings, both of which are in fluid communication with and/or provide access to the internal reservoir 50. A side opening in the housing 42 permits passage of a catheter connector 48, which is releasably connectable to the infusion catheter 44, and which is in fluid communication with the internal reservoir 50. A top opening in the housing 42 contains a self-sealing septum 46 through which the needle 20 may be removably inserted into the internal reservoir 50 for the delivery of therapeutic agents (e.g., drugs). A properly inserted needle 20 extends through the septum 46 and into the reservoir 50 of the VAP 40.

An example of a suitable VAP 40, with some modification, is disclosed in U.S. Pat. No. 5,387,192 to Glantz et al., the entire disclosure of which is incorporated herein by reference. As an option, the VAP 40 may incorporate a physiological measurement apparatus as described in U.S. patent application Ser. No. 10/246,348, entitled VASCULAR ACCESS PORT WITH PHYSIOLOGICAL SENSOR, filed on even date herewith, the entire disclosure of which is hereby incorporated by reference.

Exemplary detecting circuits 110 are described with reference to FIGS. 2-8. In these embodiments, the detecting circuit 110 may generally include a detector or sensor element and a triggering or emitting element. The triggering or emitting element may be passive (e.g., conductive, magnetic, or magnetically permeable) and separate or remote from the detecting circuit 110. The detector or sensor element may be active or passive, and may be directly or indirectly coupled to the detecting circuit 110. For each embodiment, the detector or sensor element may be carried by or incorporated into one of the needle 20 and VAP 40, and the triggering or emitting element may be carried by or incorporated into the other of the needle 20 and VAP 40.

For embodiments utilizing electrical conduction, electrical fields, or magnetic fields, the signal as detected by detecting circuit 110 may be made time varying to provide for more selective detection and to reduce the potential for adverse effects sometimes encountered when a drug is exposed to a constant electrical or magnetic field.

Figure 2:
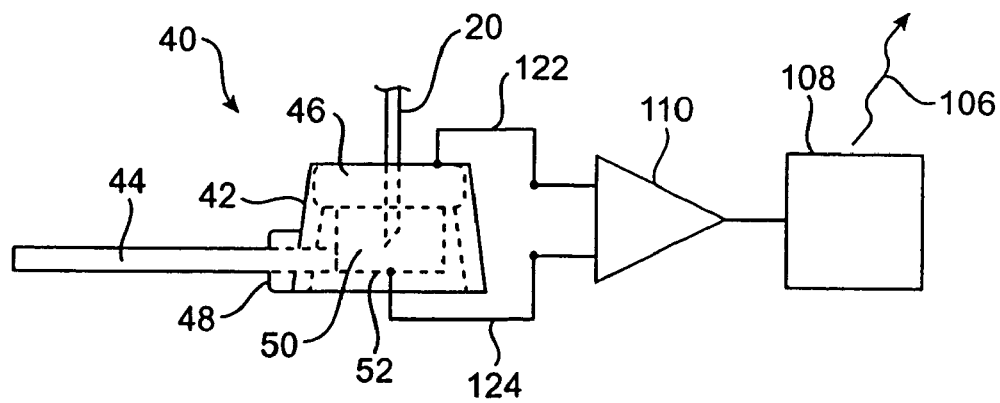
FIG. 2 is a schematic diagram of a needle detecting and indicating circuit, wherein the detecting circuit utilizes a conductive needle to detect the needle.

With reference to FIG. 2, a schematic diagram of a needle detecting circuit 110 utilizing a conductive needle 20 is shown. The needle 20 is formed of a conductive material (e.g., stainless steel) or has a conductive outer surface. The detecting circuit 110 is connected to the septum 46 of the VAP 40 and to the bottom wall 52 of the reservoir 50 by connections 122/124, respectively. The septum 46 and the reservoir bottom wall 52 are at least partially conductive such that the needle 20 makes electrical connection thereto when the needle 20 comes into contact therewith. The septum 46 may be rendered conductive by utilizing, for example, a silicone elastomer loaded with conductive material (e.g., metal particles, carbon particles, metal mesh, etc.). The bottom wall 52 may be rendered conductive by providing a conductive plate comprising stainless steel or a silicone elastomer loaded with conductive material (e.g., metal particles, carbon particles, metal mesh, etc.), for example. As an alternative, the connection 122 shown connected to the septum 46 may be connected to the needle 20, thus negating the need for a conductive septum 46.

When the needle 20 passes through the septum 46, into the reservoir 50, and comes in contact with the reservoir bottom wall 52, the needle 20 completes the circuit defined between the connections 122/124. A low power AC signal may be used in the detection circuit 110 to increase detection sensitivity and to decrease the potential for an adverse effect on the drug in the reservoir 50. In response to the completed circuit, the needle detecting circuit 110 generates a detection signal which triggers the indicating circuit 108 to generate an indicator signal 106, which is indicative of the needle 20 being properly inserted into the VAP 40. The reverse may apply when the needle 20 is removed from the reservoir 50, causing the detecting circuit 110 to modify or discontinue the detection signal which triggers the indicating circuit 108 to generate an indicator signal 106, which is indicative of the needle 20 being removed from the VAP 40.

Figure 3:
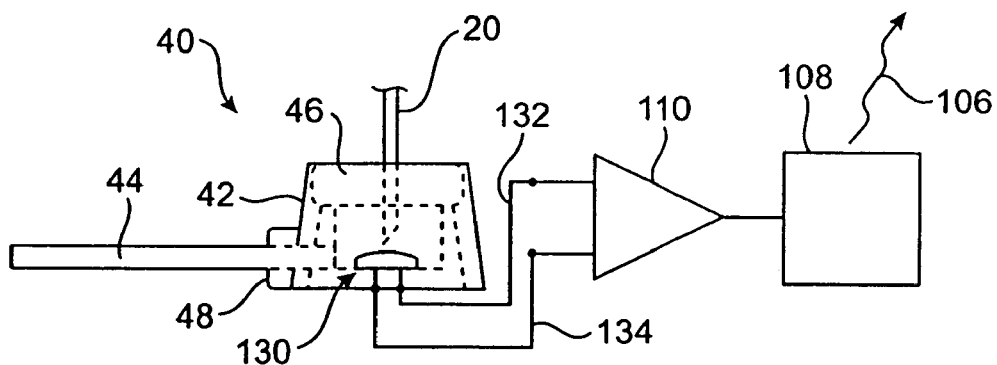
FIG. 3 is a schematic diagram of a needle detecting and indicating circuit, wherein the detecting circuit utilizes a mechanical switch to detect the needle.

With reference to FIG. 3, a schematic diagram of a needle detecting circuit 110 utilizing a mechanical switch 130 is shown. The mechanical switch 130 may, for example, be a normally-open button-type switch and may be incorporated into the bottom wall 52 of the reservoir 50 of the VAP 40. The mechanical switch 130 is connected to the detecting circuit 110 by connections 132/134.

When the needle 20 passes through the septum 46, into the reservoir 50, and contacts the reservoir bottom wall 52, the needle 20 exerts a force (e.g., downward, sideways, etc.) to close the switch 130, thus completing the circuit defined between the connections 132/134. In response to the completed circuit, the needle detecting circuit 110 generates a detection signal which triggers the indicating circuit 108 to generate an indicator signal 106, which is indicative of the needle 20 being properly inserted into the VAP 40. The reverse may apply when the needle 20 is removed from the reservoir 50, causing the detecting circuit 110 to modify or discontinue the detection signal which triggers the indicating circuit 108 to generate an indicator signal 106, which is indicative of the needle 20 being removed from the VAP 40.

Figure 4:
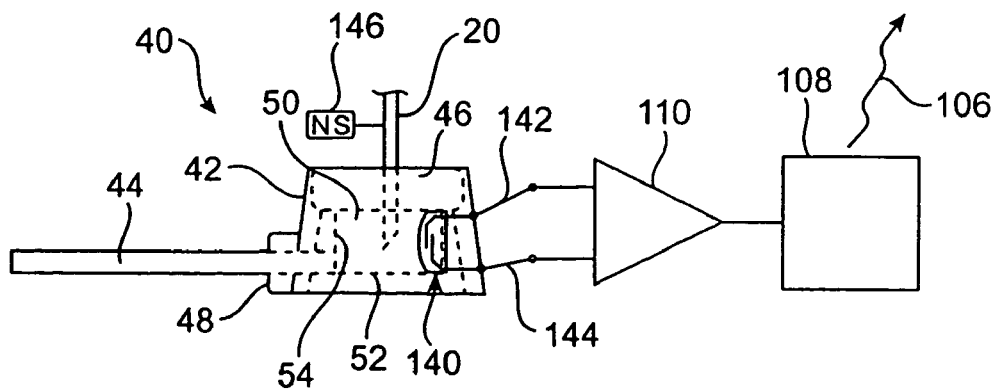
FIG. 4 is a schematic diagram of a needle detecting and indicating circuit, wherein the detecting circuit utilizes a magnetic switch to detect the needle.

With reference to FIG. 4, a schematic diagram of a needle detecting circuit 110 utilizing a magnetic switch 140 is shown. The magnetic switch 140 may, for example, be a normally-open dual reed type switch and may be incorporated into one of the side walls 54 or bottom wall 52 of the reservoir 50. The magnetic switch 140 is connected to the detecting circuit 110 by connections 142/144. The needle 20 generates a magnetic field as schematically shown by magnet 146. To this end, the needle 20 may comprise a magnetized material, such as stainless steel with sufficient ferrous content, that is rendered magnetic by carrying a tubular permanent magnet, by prolonged exposure to a magnetic field, or by a coil winding producing an electromagnet, for example.

When the needle 20 passes through the septum 46, into the reservoir 50, and comes in sufficiently close proximity to the magnetic switch 140, the magnetic field produced by the needle 20 causes the magnetic switch to close, thus completing the circuit defined between the connections 142/144. In response to the completed circuit, the needle detecting circuit 110 generates a detection signal which triggers the indicating circuit 108 to generate an indicator signal 106, which is indicative of the needle 20 being properly inserted into the VAP 40. The reverse may apply when the needle 20 is removed from the reservoir 50, causing the detecting circuit 110 to modify or discontinue the detection signal which triggers the indicating circuit 108 to generate an indicator signal 106, which is indicative of the needle 20 being removed from the VAP 40.

Figure 5:
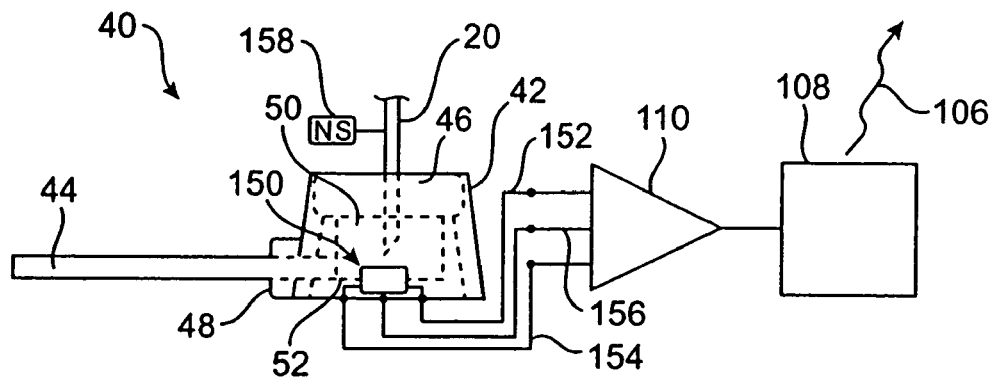
FIG. 5 is a schematic diagram of a needle detecting and indicating circuit, wherein the detecting circuit utilizes a Hall effect sensor to detect the needle.

With reference to FIG. 5, a schematic diagram of a needle detecting circuit 110 utilizing a Hall effect sensor 150 is shown. The Hall effect sensor 150 may, for example, be incorporated into the bottom wall 52 of the reservoir 50 of the VAP 40. The Hall effect sensor is connected to the detecting circuit 110 by connections 152/154/156. The needle 20 generates a magnetic field as schematically shown by magnet 158. To this end, the needle 20 may comprise a magnetized material, such as stainless steel with sufficient ferrous content, that is rendered magnetic by carrying a tubular permanent magnet, by prolonged exposure to a magnetic field, or by a coil winding producing an electromagnet, for example.

When the needle 20 passes through the septum 46, into the reservoir 50, and comes in sufficiently close proximity to the Hall effect sensor 150, movement of needle 20 and its corresponding magnetic field induces a potential difference in the Hall effect sensor 150, thus creating a potential difference across connections 152/154/156. In response to the potential difference, the needle detecting circuit 110 generates a detection signal which triggers the indicating circuit 108 to generate an indicator signal 106, which is indicative of the needle 20 being properly inserted into the VAP 40. The reverse may apply when the needle 20 is removed from the reservoir 50, causing the detecting circuit 110 to modify or discontinue the detection signal which triggers the indicating circuit 108 to generate an indicator signal 106, which is indicative of the needle 20 being removed from the VAP 4O.

Figure 6:
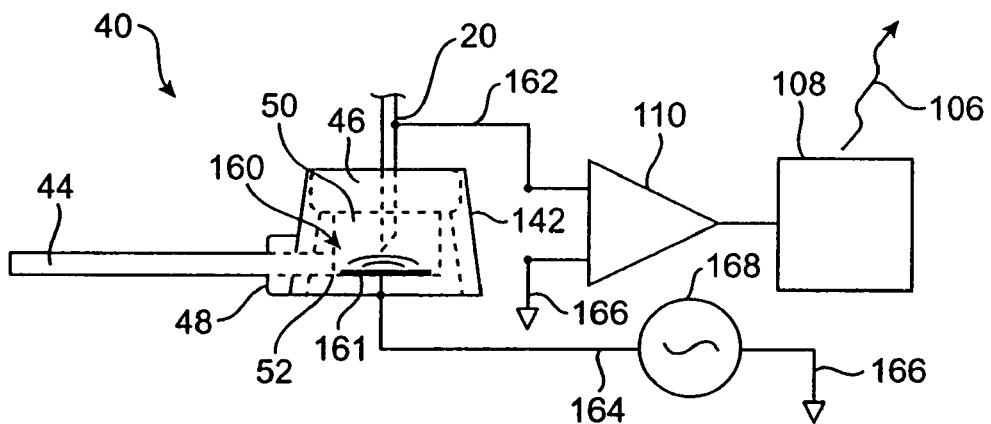
FIG. 6 is a schematic diagram of a needle detecting and indicating circuit, wherein the detecting circuit utilizes an electric field to detect the needle.

With reference to FIG. 6, a schematic diagram of a needle detecting circuit 110 utilizing an electric field 160 is shown. An electric field emitter 161 may be incorporated into the bottom wall 52 of the reservoir 50, wherein the bottom wall 52 is rendered conductive by providing a conductive plate comprising stainless steel or a silicone elastomer loaded with conductive material (e.g., metal particles, carbon particles, metal mesh, etc.), for example. The emitter 161 is connected to an electric signal generator or power source 168 by connector 164, which causes the emitter 161 to generate an electric field 160 when activated. The needle 20 is formed of a conductive material (e.g., stainless steel) or has a conductive tip, and serves as an electric field detector. The needle 20 is connected to the detection circuit 110 by connector 162. A common connection 166, utilizing ground or the patient for example, connects the signal generator 168 to the detection circuit 110. The emitter and the detector may be reversed as between the VAP 40 and the needle 20.

When the needle 20 passes through the septum 46, into the reservoir 50, and comes in close proximity to the reservoir bottom wall 52, the electric field 160 is picked up by the needle 20 and a current flow or potential is induced in the needle 20. In response to the current flow or potential in the needle 20, the detecting circuit 110 generates a detection signal which triggers the indicating circuit 108 to generate an indicator signal 106, which is indicative of the needle 20 being properly inserted into the VAP 40. The reverse may apply when the needle 20 is removed from the reservoir 50, causing the detecting circuit 110 to modify or discontinue the detection signal which triggers the indicating circuit 108 to generate an indicator signal 106, which is indicative of the needle 20 being removed from the VAP 40.

As an alternative, the connection 162 to the needle 20 may be made by providing a direct connection to the septum 46 (instead of the needle 20), and by utilizing a conductive septum 46 as described with reference to FIG. 2. In this alternative embodiment, both connections 162/164 would be connected to the VAP 40, and thus common connection 166 may be made directly as opposed to using the patient or ground as an indirect connection.

Figure 7:
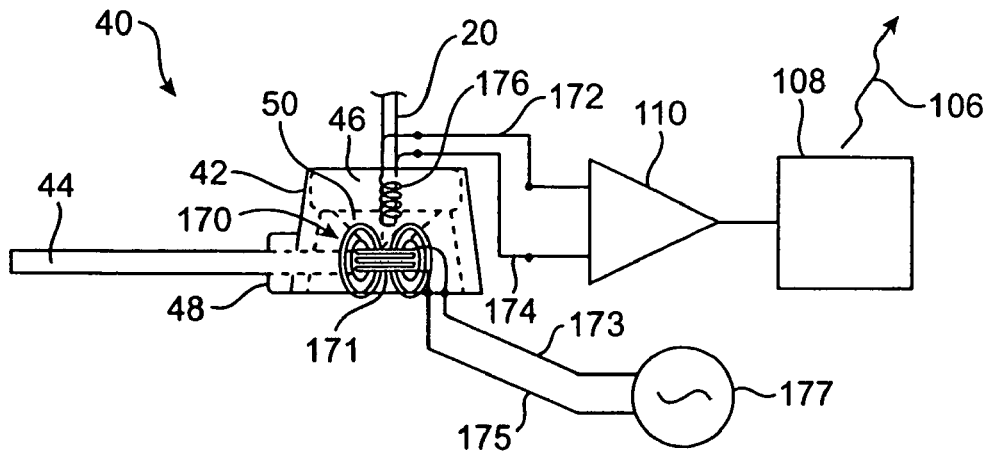
FIG. 7 is a schematic diagram of a needle detecting and indicating circuit, wherein the detecting circuit utilizes a magnetic field to detect the needle.

With reference to FIG. 7, a schematic diagram of a needle detecting circuit 110 utilizing a magnetic field 170 is shown. The magnetic field 10 may be generated by a primary coil winding 171 extending around a bottom portion of the reservoir. The primary coil winding 171 may be connected to a power source 177 via connections 173/175. The needle 20 includes a secondary coil winding 176 wound around a distal portion thereof. The secondary coil winding 176 is connected to the needle detecting circuit 110 by connections 172/174. To provide a more effective magnetic field 170, the reservoir 50 may be tapered from a larger diameter at the top to a smaller diameter at the bottom, closely matching the size of the secondary coil 176 on the needle 20.

When the needle 20 passes through the septum 46, into the reservoir 50, and the secondary coil 176 comes in close proximity to the primary coil 171, the magnetic field 170 created by the primary coil 171 induces a current flow or potential in the secondary coil 176. In response to the current flow or potential in the secondary coil 176, the detecting circuit 110 generates a detection signal which triggers the indicating circuit 108 to generate an indicator signal 106, which is indicative of the needle 20 being properly inserted into the VAP 40. The reverse may apply when the needle 20 is removed from the reservoir 50, causing the detecting circuit 110 to modify or discontinue the detection signal which triggers the indicating circuit 108 to generate an indicator signal 106, which is indicative of the needle 20 being removed from the VAP 40.

Figure 8:
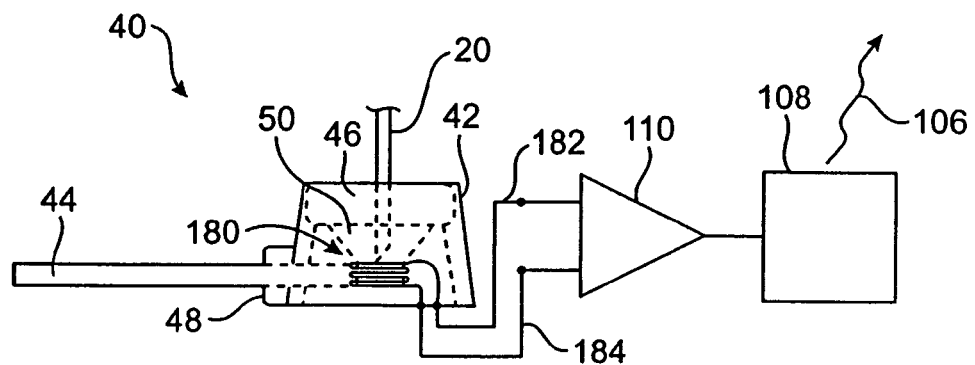
FIG. 8 is a schematic diagram of a needle detecting and indicating circuit, wherein the detecting circuit utilizes an inductor to detect the needle.

With reference to FIG. 8, a schematic diagram of a needle detecting circuit 110 utilizing an inductor 180 is shown. Inductor 180 may comprise a coil winding as shown and may be connected to the detecting circuit 110 by connections 182/184. The needle 20 may comprise a magnetically permeable material such as a stainless steel with sufficient ferrous content.

When the needle 20 passes through the septum 46, into the reservoir 50, and comes in close proximity to the inductor 180, the needle 20 changes the inductance of the inductor 180. In response to the change in inductance, the detecting circuit 110 generates a detection signal which triggers the indicating circuit 108 to generate an indicator signal 106, which is indicative of the needle 20 being properly inserted into the VAP 40. The reverse may apply when the needle 20 is removed from the reservoir 50, causing the detecting circuit 110 to modify or discontinue the detection signal which triggers the indicating circuit 108 to generate an indicator signal 106, which is indicative of the needle 20 being removed from the VAP 40.

In clinical practice, not only is it useful to know if the needle 20 has been properly inserted in the VAP 40 and if it has been maintained as such, but it is also useful to know whether the infusion catheter 44 of the VAP 40 is blocked or partially blocked, and if the pump is delivering drug to the patient. One approach to addressing this issue is to measure pressure in the blood vessel where the infusion catheter 44 is placed relative to the pressure in the port reservoir 50. If the infusion catheter 44 is open and there is normal flow of drug, the pressure in the blood vessel at the distal end of the infusion catheter 44 will be somewhat lower than that in the reservoir due to fluid flow and pressure drop in the small infusion catheter 44. If the infusion catheter 44 starts to become blocked, pressure in the reservoir 50 will rise and become significantly higher relative to the blood vessel adjacent the distal end of the infusion catheter 44. If the catheter is completely blocked, the relative pressure in the reservoir 50 will reach the delivery pressure of the infusion pump.

Figure 9:
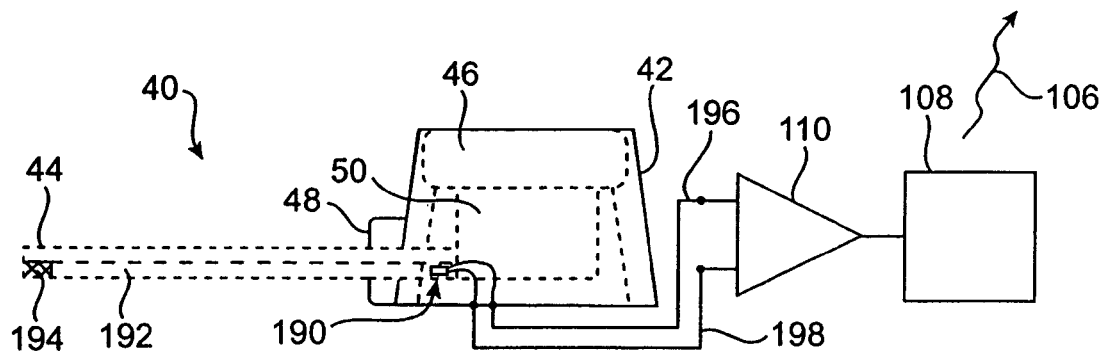
FIG. 9 is a schematic diagram of a detecting and indicating circuit, wherein the detecting circuit utilizes a pressure or flow sensor to detect the needle and/or a clogged infusion catheter.

With reference to FIG. 9, a schematic diagram of a detecting circuit 110 utilizing a pressure sensor 190 is shown. The infusion catheter 44 of the VAP 40 includes an additional lumen 192 containing a fluid and a distal gel plug 194. The additional lumen refers the intravascular pressure adjacent the distal end of the infusion catheter 44 to pressure sensor 190. The pressure sensor 190, fluid filled lumen 192 and gel plug 194 are similar to that which is disclosed in U.S. Pat. No. 4,846,191 to Brockway et al., the entire disclosure of which is hereby incorporated by reference. The pressure sensor 190 is connected to the detecting circuit 110 by connections 196/198.

In response to a decrease in distal pressure relative to the reservoir pressure as measured by sensor 190, the detecting circuit 110 generates a detection signal which triggers the indicating circuit 108 to generate an indicator signal 106(+), which is indicative of the needle 20 being properly inserted into the VAP 40 and adequate flow through the infusion catheter 44. In response to a further decrease in distal pressure relative to the reservoir pressure (due to an increase in reservoir pressure) as measured by sensor 190, the indicating circuit 108 may generate an indicator signal 106(−) which is indicative of the infusion catheter 44 being clogged.

As an alternative to pressure sensor 190, a flow sensor may be used. Fluid flow may be measured using ultrasound (Doppler or transit time techniques) or by using a thermal dilution technique. In this alternative embodiment, a small heater element may be placed upstream and a temperature sensor may be placed downstream in the infusion catheter 44, with a small amount of pulsed energy delivered to the heater element. The temperature sensor would measure the change in temperature and from this an assessment of flow could be derived, in a manner similar to the techniques used to measure cardiac output with a thermal dilution catheters.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A system comprising:
   a vascular access port including a portal housing containing an internal reservoir with first and second openings, a self-sealing septum disposed in the first opening, and a catheter extending from the portal housing, the catheter defining a lumen extending therethrough in fluid communication with the reservoir via the second opening;
   a magnetic needle;
   a Hall effect sensor comprising a plurality of Hall effect sensor connections, the Hall effect sensor producing a potential difference across the Hall effect sensor connections in response to an experienced magnetic field; and
   a detecting circuit electrically connected to the Hall effect sensor connections so as to detect the presence or absence of the magnetic needle in the reservoir.

2. The system of claim 1, wherein detecting circuit is connected to an infusion pump and provides feedback thereto.

3. The system of claim 1, wherein the detecting circuit generates a detection signal indicative of a proximity of the needle to the reservoir.

4. The system of claim 1, further comprising a magnet.

5. The system of claim 4, wherein the magnet is carried by the needle.

6. The system of claim 5, wherein the detecting circuit generates a detection signal when the Hall effect sensor is in close proximity to the magnet, and wherein the proximity is indicative of the needle extending into the reservoir.

7. The system of claim 1, wherein the detecting circuit generates a detection signal in response to a potential difference across the Hall effect sensor connections.

8. The system of claim 1, wherein:
   the detecting circuit includes a comparator that compares the potential difference across the Hall effect sensor connections to a threshold signal value that is indicative of the needle extending into the reservoir, and
   the detecting circuit generates an insertion signal when the potential difference across the Hall effect sensor connections exceeds the threshold signal value.

9. The system of claim 1, wherein the Hall effect sensor is incorporated into a wall of the reservoir.

10. The system of claim 1, further comprising a permanent magnet attached to the needle.

11. The system of claim 1, wherein the needle is rendered magnetic by a permanent magnet.

12. The system of claim 1, wherein the needle that is rendered magnetic by a coil producing an electro-magnet.

13. A vascular access port system for detecting the presence or absence of a needle, the system comprising:
   a vascular access port including a portal housing containing an internal reservoir with first and second openings, a self-sealing septum disposed in the first opening, and a catheter extending from the portal housing, the catheter defining a lumen extending therethrough in fluid communication with the reservoir via the second opening;
   a Hall effect sensor incorporated into a wall of the reservoir;
   a needle generating a magnetic field; and
   a detecting circuit connected to the Hall effect sensor, the detecting circuit generating a detection signal in response to changes in a potential difference across the Hall effect sensor.

14. The system of claim 13, wherein the needle is rendered magnetic by a permanent magnet.

15. The system of claim 13, wherein the potential difference across the Hall effect sensor changes when the Hall effect sensor is exposed to the magnetic field produced by the needle.

16. The system of claim 13, wherein the potential difference across the Hall effect sensor changes when the needle is in close proximity to the Hall effect sensor.

17. The system of claim 13, further comprising a permanent magnet carried by the needle.

18. The system of claim 13, wherein the needle and a coil produce an electro-magnet.

* * * * *

UNITED STATES PATENT AND TRADEMARK OFFICE
CERTIFICATE OF CORRECTION

PATENT NO. : 7,347,843 B2  Page 1 of 1
APPLICATION NO. : 11/190789
DATED : March 25, 2008
INVENTOR(S) : H. Clark Adams et al.

It is certified that error appears in the above-identified patent and that said Letters Patent is hereby corrected as shown below:

Column 10, line 28 (claim 12), delete "that"

Signed and Sealed this

Twenty-third Day of June, 2009

JOHN DOLL
*Acting Director of the United States Patent and Trademark Office*